US008927524B2

(12) United States Patent
Bender et al.

(10) Patent No.: US 8,927,524 B2
(45) Date of Patent: Jan. 6, 2015

(54) STERILE ALGINATE-BASED AQUEOUS COMPOSITION FOR MEDICAL USE AND PROCESS FOR THE PREPARATION THEREOF

(75) Inventors: Johannes Caspar Mathias Elizabeth Bender, Utrecht (NL); Hubert Clemens Pellikaan, Utrecht (NL)

(73) Assignee: Bender Analytical Holding B.V., Utrecht (NL)

( * ) Notice: Subject to any disclaimer, the term of this patent is extended or adjusted under 35 U.S.C. 154(b) by 295 days.

(21) Appl. No.: 13/583,912

(22) PCT Filed: Mar. 8, 2011

(86) PCT No.: PCT/NL2011/050160

§ 371 (c)(1), (2), (4) Date: Dec. 18, 2012

(87) PCT Pub. No.: WO2011/112082

PCT Pub. Date: Sep. 15, 2011

(65) Prior Publication Data

US 2013/0096080 A1 Apr. 18, 2013

(30) Foreign Application Priority Data

Mar. 11, 2010 (EP) .................................... 10156259

(51) Int. Cl.

| | |
|---|---|
| ***A61K 31/734*** | (2006.01) |
| ***A61K 9/00*** | (2006.01) |
| ***A61K 47/02*** | (2006.01) |
| ***A61K 47/36*** | (2006.01) |

(52) U.S. Cl.

CPC ............. *A61K 31/734* (2013.01); *A61K 9/0024* (2013.01); *A61K 47/02* (2013.01); *A61K 47/36* (2013.01)

USPC ........................................................... 514/54

(58) Field of Classification Search

None

See application file for complete search history.

(56) References Cited

U.S. PATENT DOCUMENTS 5,693,624 A * 12/1997 Hardy et al. .................... 514/54
6,638,917 B1 10/2003 Li et al.

FOREIGN PATENT DOCUMENTS

KR 2001-0107067 A 12/2001

OTHER PUBLICATIONS

Database WPI, Week 200256, Thomson Scientific, London, GB; AN 2002-525366, XP002592273, & KR 2001 107 067 A (Amitie Co Ltd)Dec. 7, 2001 abstract.

Holme H K et al: "Kinetics and mechanisms of depolymerization of alginate and chitosan in aqueous solution", Carbohydrate Polymers, Applied Science Publishers, Ltd. Barking, GB, vol. 73, No. 4, Sep. 5, 2008, paged 656-664, XP022664472.

International Preliminary Report on Patentability for PCT/NL2011/050160—mailed Jun. 1, 2012.

International Search Report for PCT/NL2011/050160—mailed May 30, 2011.

* cited by examiner

*Primary Examiner* — Layla Bland

(74) *Attorney, Agent, or Firm* — Gilberto M. Villacorta; Sunit Talapatra; Foley & Lardner LLP

(57) ABSTRACT

The present invention relates to ready-to-use sterile, alginate-based, aqueous compositions for medical use. More particularly, the invention relates to an aqueous composition for medical use that has been sterilized by heat sterilization and having a viscosity at 25° C. of at least 300 cP) (Helipath® T F spindle, 100 rpm at 25° C.), said composition having a pH in the range of 6.5-7.5; containing 0.5-10 wt. % of an alginate salt; and further containing 10-500 mM of one or more dissolved $C_2$-$C_7$ mono- or dicarboxylates that are optionally substituted with up to 2 hydroxyl groups.

The alginate-based composition of the present invention has excellent storage stability and is easy to manufacture. The alginate-based aqueous compositions of the present invention can advantageously be used, for instance, to prevent adhesions between a healing trauma site and adjacent surrounding tissue. These compositions can further be used in implants or in pharmaceutical preparations for oral administration.

18 Claims, No Drawings

STERILE ALGINATE-BASED AQUEOUS COMPOSITION FOR MEDICAL USE AND PROCESS FOR THE PREPARATION THEREOF

CROSS-REFERENCE TO RELATED APPLICATIONS

This application is a National Phase of International Application PCT/NL2011/050160, filed Mar. 8, 2011, which was published on Sep. 15, 2011, as WO 2011/112082 A1, which claims the benefit of EP Appln No. 10156259.3, filed Mar. 11, 2010, all of which are incorporated herein by reference in their entirety.

TECHNICAL FIELD OF THE INVENTION

The present invention relates to sterile alginate-based aqueous compositions for medical uses. The alginate-based aqueous compositions of the present invention can advantageously be used, for instance, to prevent adhesions between a healing trauma site and adjacent surrounding tissue. These compositions can further be used in implants or in pharmaceutical preparations for oral administration.

The invention further relates to a process for the preparation of such aqueous alginate-based compositions.

BACKGROUND OF THE INVENTION

Adhesions are unwanted tissue growths occurring between layers of adjacent bodily tissue or between tissues and internal organs. Adhesions are often formed during the dynamic process of healing of the incision and tissue trauma after surgery. The initiation of the adhesion begins with the formation of a fibrin matrix. The ischemic conditions caused by surgery prevent fibrinolytic activity to dissolve the matrix, and the fibrin persists. Wound repair cells then turn the matrix into an organized adhesion, often having a vascular supply and neuronal elements. Adhesions can prevent the normal motions of tissues and organs with respect to their neighbouring structures. Adhesions are a particular problem in gastrointestinal and gynecological surgery, leading to post-operative bowel obstruction, infertility, and chronic pelvic pain.

The medical and scientific communities have studied ways of reducing the formation of post-surgical adhesions by the use of high molecular weight carboxyl-containing biopolymers. These biopolymers can form hydrated gels which act as physical barriers to separate tissues from each other during healing, so that adhesions between normally adjacent structures do not form. After healing is substantially complete, the barrier is no longer needed, and should be eliminated from the body to permit more normal function of the affected tissues.

KR 2001 107 067 describes an adhesion preventing agent comprising 1.0-15 wt % of alginate having a viscosity of 150 centipoise, 0-2.5 wt % of polyethylene glycol having a molecular weight of 3,000-5,000, 0-8 wt % of agarose, 0-1 wt. % of an antibiotic, and 73.5-99.0 wt % of water. The adhesion preventing agent is sterilized at a temperature of less than 150° C. for 5-20 minutes.

U.S. Pat. No. 6,150,581 (United States Surgical Corporation) describes a method for preventing post surgical adhesions comprising:

providing an aqueous solution of chitosan and a complexing agent;

providing an aqueous solution of alginate; and combining the chitosan/complexing agent solution with the alginate solution to form an anti-adhesion barrier at a site of surgical intervention.

U.S. Pat. No. 6,638,917 (Boston Scientific SciMed, Inc) describe a method of forming a sheet for use as an adhesion barrier, comprising:

forming a film from an alginate solution; and contacting the film with a cross-linking solution to form a cross-linked mechanically stable sheet for placement of at least a portion of the sheet at a site of trauma to create the adhesion barrier WO 2006/044342 A2 (FMC Biopolymer AS) describes a method of using a self gelling alginate dispersion to prevent post surgical adhesion formation in an individual, said method comprising dispensing a self gelling alginate dispersion within an individual by:

a) forming a dispersion by mixing i) a solution comprising a soluble alginate with an insoluble alginate/gelling ion particles or ii) immediately soluble alginate, insoluble alginate/gelling ion particles and a solvent, and b) dispensing the dispersion whereby the dispersion forms an alginate gel matrix.

The present invention aims to provide a sterile, ready-to-use alginate-based aqueous composition of neutral pH that has excellent storage stability, that can be directly applied as such at the site of trauma, and that is easy to manufacture. In particular, the present invention relates to a sterile alginate-based aqueous gel formulation that can be produced using heat sterilization of the total composition and that is heat stable as well as storage stable in terms of pH and rheological properties (e.g. viscosity).

SUMMARY OF THE INVENTION

The inventors have discovered that the aforementioned desirable features can be realized in an alginate-based aqueous composition that has been sterilized by heat sterilization and that contains 0.5-10 wt. % of an alginate salt and 10-500 mM of one or more dissolved $C_2$-$C_7$ mono- or dicarboxylates that are optionally substituted with up to 2 hydroxyl groups, said alginate-based composition further being characterized by a pH of 6.5-7.5 and a viscosity at 25° C. of at least 300 cP.

The specifications for alginate-based compositions have to be very tight given that these compositions are often applied in critically ill patients and furthermore, because they are applied directly at the site of surgical trauma. However, meeting such tight specifications poses a major challenge in case the composition is alginate-based.

It is known from e.g. Holme et al. 2008 (*Kinetics and mechanisms of depolymerization of alginate and chitosan in aqueous solution*. Carbohydrate Polymers 2008, Vol. 73, 656-664), Home et al. 2003 (*Thermal depolymerization of alginate in the solid state*. Carbohydrate Polymers 2003, Vol. 54, 431-438.) and Bradley et al. (*The Determination of Kinetics of Polysaccharide Thermal Degradation using High Temperature Viscosity Measurements*. Carbohydrate Polymers 1988, Vol. 9, 257-267) that both heat sterilization and storage induce decomposition of alginate, resulting in time-dependent changes of pH and viscosity.

The inventors have also found that heat sterilization, especially moist heat sterilization above 100° C., tends to adversely effect both the pH-stability and rheological stability of alginate-based aqueous compositions. Investigations undertaken by the inventors ultimately showed that this particular instability was somehow linked to the buffering systems (e.g. phosphate buffers) that are used to render these compositions biocompatible. In addition, the inventors have unexpectedly discovered that alginate-based aqueous compositions of neutral pH containing 0.01-0.5M of one or more dissolved $C_2$-$C_7$ mono- or dicarboxylates do not suffer from this instability and that alginate-based compositions that are buffered by these carboxylates can suitably be heat sterilized. Examples of $C_2$-$C_7$ mono- or dicarboxylates that may suitably be employed include acetate, propionate, fumarate, tartarate and benzoate.

U.S. Pat. No. 5,693,624 (Johnson & Johnson Medical Inc.) describes an aqueous gel composition for use as a wound dressing comprising from 2% to 10% w/v of a water-soluble alginate salt and from 1% to 40% w/v of a $C_3$-$C_6$ dihydric or trihydric alcohol, said composition being substantially sterile and having been sterilized by heat sterilization. In the US patent it is stated that the inclusion of relatively large amount of polyhydric alcohol (more than 15% w/v) results in an alginate gel that is stabilised against hydrolysis and consequent loss of viscosity during autoclave sterilization.

The present invention also provides a process for preparing an alginate-based aqueous composition as described above, said process comprising combining a water-soluble alginate salt; the one or more $C_2$-$C_7$ mono- or dicarboxylates and water, followed by heat sterilization

DETAILED DESCRIPTION OF THE INVENTION

Accordingly, one aspect of the invention relates to an aqueous alginate-based composition that has been sterilized by heat sterilization and having a viscosity at 25° C. of at least 300 cP (Helipath® T F spindle, 100 rpm), said composition having a pH in the range of 6.5-7.5; containing 0.5-10 wt. % of an alginate salt; and further containing 10-500 mM of one or more dissolved $C_2$-$C_7$ mono- or dicarboxylates that are optionally substituted with up to 2 hydroxyl groups.

Whenever reference is made in this document to a "$C_n$, monocarboxylate", what is meant is a monocarboxylate substance that contains n carbon atoms, including the carbon atom of the carboxyl group. Likewise, the term "$C_n$, dicarboxylate" refers to a dicarboxylate substance that contains n carbon atoms, including the two carbon atoms of the carboxyl groups. Thus, acetate is an example of a $C_2$ monocarboxylate and succinate is an example of a $C_4$ dicarboxylate.

Although the inventors do not wish to be bound by theory, it is believed that the $C_2$-$C_7$ mono- or dicarboxylates act as buffering agents. Here the term "buffering agent" refers to substances that can be used in aqueous systems to drive an acidic or basic solution to a certain pH (e.g. a pH within the range of 6.5-7.5) and that prevent a change in this pH.

Buffering agents can be either the weak acid or weak base that would comprise a buffer solution (an aqueous solution comprising a mixture of a weak acid and its conjugate base or a weak base and its conjugate acid). Buffering agents are the substances that are responsible for the buffering seen in buffer solutions. Buffering agents are similar to buffer solutions in that buffering agents are the main components of buffer solutions. They both regulate the pH of a solution and resist changes in pH. A buffer solution maintains the pH for the whole system which is placed into it, whereas a buffering agent can be added to an already acidic or basic solution, which it then modifies and maintains a new pH.

Typically, the alginate-based composition has a viscosity at 25° C. of not more than 10,000 cP. Preferably, said viscosity lies within the range of 500-8,000 cP, even more preferably of 700-4,000 cP. The alginate-based composition advantageously has a sufficiently high viscosity to prevent it from flowing away from the trauma site and a sufficiently low viscosity to allow it to spread out over the trauma site.

The altginate-based composition of the present invention offers the advantage that it is ready-for-use and that it is a single component system, as opposed to some of the two-component systems described in the prior art. The present composition can be a viscous liquid or a gel that can be rendered flowable by applying pressure or shear (e.g. a thixotropic gel).

Alginates are hydrophilic biopolymers with the unique ability to form heat-stable gels that can develop and set at physiologically relevant temperatures. Alginates are a family of non-branched binary copolymers of 1-4 glycosidically linked β-D-mannuronic acid (M) and α-L-guluronic acid (G) residues. The relative amount of the two uronic acid monomers and their sequential arrangement along the polymer chain vary widely, depending on the origin of the alginate. Alginate is the structural polymer in marine brown algae such as *Laminaria hyperborea, Macro cystis pyrifera, Lessonia nigrescens* and *Ascophyllum nodosum*. Alginate is also produced by certain bacteria such as *Pseudomonas aeruginosa, Azotobacter vinelandii* and *Pseudomonas fluoresceins* (WO 04/011628).

The present invention utilizes an alginate salt, preferably an alginate metal salt. Even more preferably, the alginate salt comprises one or more cations selected from $Na^+$, $K^+$, $Ca^{2+}$ and $Mg^{2+}$.

The amount of alginate salt contained in the present alginate-based composition preferably lies within the range of 1-5 wt. %. Most preferably, the alginate salt content of the composition is in the range of 1.2-4 wt. %.

Best results are obtained with the present alginate-based composition if the a high molecular weight alginate salt is employed. Accordingly, the alginate salt advantageously has a molecular weight of at least 50,000 g/mol, even more preferably of at least 400,000 g/mol.

The present aqueous composition can advantageously be used as an anti-adhesion composition. Alternative medical applications include the use as an implant or as an oral dosage unit. Especially in case of the latter applications, the aqueous composition advantageously contains a pharmaceutically active ingredient. It will be understood that for the aforementioned medical applications it is highly desirable to employ an ultrapure alginate, i.e. an alginate from which endotoxins have been removed almost completely. Preferably, the alginate employed in accordance with the present invention is an alginate that meets the standard laid down in ASTM F2064-00 (reapproved 2006).

It is well-known that alginate gels can be produced when a multivalent cation (e.g. $Ca^{2+}$) forms ionic bonds with the negatively charged group from a G residue from two or more different alginate polymers, thereby cross-linking these polymers. The formation of multiple cross-linkages among numerous alginate polymers results in the matrix that is the alginate gel structure.

According to a preferred embodiment at least a part of the alginates salt contained in the alginate-based composition is cross-linked by divalent cations selected from $Ca^{2+}$, $Mg^{2+}$ and combinations thereof. Advantageously, the alginate in the present composition is only moderately cross-linked in order to prevent the composition from becoming a rigid gel. Typically, the total content of divalent cations selected from $Ca^{2+}$, $Mg^{2+}$ and combinations thereof is within the range of 10-3000 μmol per gram of alginate, more preferably 20-1200 μmol per gram of alginate per gram of alginate and most preferably 40-800 μmol per gram of alginate per gram of alginate. Moderate cross-linking of the alginate was found to reduce the pH drift observed during sterilisation. Furthermore, the inventors have observed that such cross-linking improves stability of pH and viscosity during storage.

The total content of monovalent cations selected from $Na^+$, $K^+$ and combinations thereof preferably lies within the range of 0.5-50 mmol, more preferably 1-30 mmol and most preferably 2-20 mmol per gram of alginate The amount of the one or more $C_7$-$C_7$ mono- or dicarboxylates employed in the present alginate-based composition preferably lies within the range of 15 to 400 mmol/l. Even more preferably, the amount of buffering agent is within the range of 20-300 mmol/l.

The $C_2$-$C_7$ mono- or dicarboxylates may be saturated or unsaturated, linear or cyclic. In accordance with a preferred embodiment of the present invention, the one or more mono- or dicarboxylates are saturated or unsaturated, linear $C_2$-$C_4$ mono- or dicarboxylates that are optionally substituted with up to 2 hydroxyl groups. More preferably, the one or more carboxylates are saturated, linear $C_7$-$C_4$ mono- or dicarboxylates that are substituted with up to 2 hydroxyl groups. Even more preferably, the one or more carboxylates are unsubstituted, saturated, linear $C_2$-$C_4$ mono- or dicarboxylates, especially unsubstituted, saturated, linear $C_2$-$C_4$ monocarboxylates, e.g. acetate, propionate.

According to another advantageous embodiment, the $C_2$-$C_7$ mono- or dicarboxylates are aromatically unsaturated cyclic $C_7$ monocarboxylates, e.g. benzoate.

According to a particularly preferred embodiment of the present invention, the one or more $C_2$-$C_7$ mono- or dicarboxylates employed in the alginate-based composition are represented by the following formula:

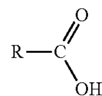

wherein R represents $R^1(R^2)CH$; $R^3$—CH═CH or fenyl;

$R^1$ representing hydrogen or hydroxyl;

$R^2$ representing hydrogen or $R^4(R^5)CH$;

$R^3$ representing methyl or COOH;

$R^4$ representing hydrogen or hydroxyl; and $R^5$ representing hydrogen or COOH.

Examples of $C_2$-$C_7$ mono- or dicarboxylates encompassed by the aforementioned formula include: acetate, propionate, crotonate, succinate, fumarate, tartarate and benzoate.

In accordance with one advantageous embodiment of the invention the carboxylate employed is represented by the aforementioned formula wherein R represents $R^1(R^2)CH$. Examples of such mono- or dicarboxylates include acetate, propionate succinate, and tartarate. More preferably, $R^1$ represents hydrogen and $R^2$ represents hydrogen, $CH_3$, $CH_2COOH$ or CH(OH)COOH. According to a particularly preferred embodiment, the one or more carboxylates are selected from acetate ($R^1$═H; $R^2$═H) and propionate ($R^1$═H; $R^2$=methyl). Most preferably, the carboxylate is acetate.

According to a particularly advantageous embodiment of the present invention, the alginate-based composition comprises acetate in combination with 0.1-5 mM of dissolved carbonate. The inventors have discovered that the use of this particular combination of buffering agents offers the advantage that the pH drop that is normally observed during heat sterilization of the composition can be minimized effectively. In the alginate-based composition acetate and carbonate are preferably employed in a molar ratio of 10:1 to 250:1, more preferably in a molar ratio of 20:1 to 200:1.

In accordance with another advantageous embodiment the carboxylate contained in the aqueous composition is benzoate. The inventors have found that benzoate can be used produce an alginate-based composition whose pH remains remains virtually unchanged during sterilisation and subsequent storage.

Yet another beneficial embodiment relates to an aqueous composition in which the mono- or dicarboxylates employed are represented by the aforementioned formula wherein R represents $R^3$—CH═CH. The carboxylates encompassed are fumarate and crotonate.

As explained herein before, the alginate-based composition of the present invention offers the important advantage that its pH remains stable during storage, even when the product is stored at elevated temperatures. Accordingly, in accordance with another preferred embodiment, the pH of the composition remains within the range of 6.5-7.5 when the composition is kept at 40° C. for 6 months.

In order to ensure that, for instance, atmospheric carbon dioxide will not influence the pH of the alginate-based composition, said composition is preferably packaged without a headspace or with a headspace that contains no carbon dioxide. Even more preferably, the headspace contains an inert gas such as nitrogen.

The alginate-based composition of the present invention is surprisingly stable under sterilization conditions, notably moist heat sterilization at temperatures well above 100° C. This characteristic is evident from the fact that the composition can be heated to high temperature for a significant amount of time without resulting in a substantial viscosity decrease and/or pH change. Thus, a preferred alginate-based composition meets the condition that its viscosity at 25° C. of the aqueous composition does not drop by more than 50% if the aqueous composition is heated to 121° C. for 15 minutes.

The bulk of the present alginate-based aqueous composition consists of water. Typically, the alginate-based composition contains 95-99 wt. % of water.

Besides the alginate salt, the one or more $C_2$-$C_7$ mono- or dicarboxylates and the water, the alginate-based composition may suitably contain other components, such a pharmaceutically active substances (e.g. antimicrobials, anti-inflammatories), dextran sulphate, dermatan sulphate, pentosan polysulphate, sodium chloride etc.

To limit the alginate's tendency to promote the growth of intra-abdominal anaerobic bacteria, possibly leading to intra-abdominal abcess formation or causing localized peritonitis to develop into generalized peritonitis, the alginate based composition advantageously contains a biocompatible antimicrobial agent, to inhibit growth of intra-abdominal anaerobic bacteria.

The aqueous alginate-based composition of the present invention, unlike the sterile wound dressing compositions described in U.S. Pat. No. 5,693,624, preferably contains less than 15% (w/v) of polyhydric alcohol, e.g. a C3-C6 polyhydric alcohol such as propylene glycol or hexylene glycol. Even more preferably the alginate-based composition contains less than 10% (w/v), most preferably less than 1% (w/v) polyhydric alcohol.

Likewise, the alginate-based composition of the present invention, unlike the adhesion preventing agent taught by KR 2001 107 067 does not contain polyethylene glycol having a molecular weight of 3,000-5,000.

The aqueous alginate-based composition preferably is more or less isotonic. Thus, the alginate-based composition preferably contains $C^-$ in a concentration of 20-300 mmol/l, more preferably in a concentration of 50-250 mmol/l.

Another aspect of the invention relates to a process for preparing an alginate-based aqueous composition as defined herein before, said process comprising combining a water-soluble alginate salt; the one or more $C_2$-$C_7$ mono- or dicarboxylates and water, followed by moist heat sterilisation.

Preferably, the sterilization conditions employed in the present process achieve a sterility assurance level of less than $10^{-5}$, more preferably of less than $10^{-6}$.

In the present process heat sterilisation is suitably achieved by heating to a temperature of at least 100° C. for at least 5 minutes. Even more preferably, said heat sterilization involves heating to a temperature of at least 110° C. for at least 5 minutes, more preferably for at least 10 minutes. Most preferably, the heat sterilization involves heating to a temperature of at least 115° C. for at least 5 minutes, especially at least 10 minutes.

According to a particularly preferred embodiment, the moist heat sterilization employs high pressure steam. Even more preferably, the moist heat sterilization is carried out in an autoclave.

As explained herein before, preferably at least some of the alginate salt is cross-linked by multivalent (metal) cations. Advantageously this cross-linking is achieved by combining an aqueous solution of the alginate salt with an aqueous solution containing multivalent cations. More particularly, the present process advantageously comprises combining an aqueous solution of 6-120 g/l of the water-soluble alginate salt with an aqueous solution containing 3-250 mmol/l of divalent cations selected from $Ca^{2+}$, $Mg^{2+}$ and combinations thereof. According a particularly preferred embodiment, the aqueous solution of the water-soluble alginate salt and the aqueous solution of the divalent cations are combined in a weight ratio that lies within the range of 1:2 to 10:1. Preferably, the one or more $C_2$-$C_7$ mono- or dicarboxylates are contained in the aqueous solution of the water-soluble alginate salt.

The present invention offers the advantage that pH of the alginate-based composition not only remains stable after heat sterilization, but also that the pH hardly changes during sterilization. Typically, the pH change observed during sterilization is less than 1.0 pH-unit, more preferably less than 0.5 pH-unit. Generally speaking, during sterilization the pH of the alginate-based composition remains within the range of 6.5-7.5

The invention is further illustrated by means of the following non-limiting examples.

EXAMPLES

Example 1

This Example demonstrates the influence of different buffering agents on the pH and viscosity of heat sterilized alginate-based aqueous compositions.

Alginate-based aqueous compositions (100 ml) were prepared on the basis of the following recipe:

| Ingredient | Amount |
|---|---|
| Sodium alginate[#] | 2200 mg |
| $CaCl_2$ | 1.6 mg |
| Dextran sulphate | 53.8 mg |
| NaCl | 806 mg |
| Buffering agent | Specified below |
| Water | Remainder (to 100 ml) |

[#]Manugel ® DMB, high G alginate (visc. 300 cP; 1% aq. solution), ex FMC BioPolymer The alginate-based aqueous compositions were compounded with the following physiologically acceptable buffers to produce a buffered composition having a pH of 7.50:

citrate (270 mg of sodium citrate)
phosphate (67 mg of $NaH_2PO_4$ and 220 mg of $Na_2HPO_4$)
acetate (270 mg of sodium acetate)
carbonate (270 mg of sodium bicarbonate)

In addition, a reference composition containing no buffering agent was prepared. In all cases pH was adjusted to 7.5 with the help of 0.1N NaOH or 0.1N HCl.

Buffer compositions were made by accurately weighing the ingredients into the mixing flask and making up to volume with water for injection. Sodium chloride and dextran sulfate were then added to the buffer solution and dissolved. Ultrapure sodium alginate was then mixed into the solution to afford a homogeneous clear gel. A second solution containing the chosen buffer and calcium chloride was made after which it was combined with the gel.

Subsequently, the alginate-based aqueous compositions were sterilized by steam sterilisation (30 minutes at 121° C.). This sterilisation process is a worst case challenge. Normal sterilisation conditions to achieve SAL (sterility assurance level) of $10^{-4}$ is heating at 121° C. for 15 minutes.

After sterilization, the viscosity of the different buffered alginate-based aqueous compositions at 25° C. was determined at 100 rpm, using a Helipath® T F spindle. Also the viscosity of the reference composition was determined, both before and after sterilization. Likewise, the pH of the buffered compositions was measured after sterilization and the pH of the reference composition was determined before and after sterilization.

The data so obtained are depicted in the following table

| | Before sterilization | | After sterilization | |
|---|---|---|---|---|
| Buffering agent | Viscosity | pH | Viscosity | pH |
| Citrate | 600 | 7.5 | 100 | 6.56 |
| Phosphate | 600 | 7.5 | <50 | 6.05 |
| Acetate | 600 | 7.5 | 250 | 6.37 |
| Carbonate | 600 | 7.5 | 125 | 8.66 |
| Reference | 600 | 7.5 | 500 | 5.74 |

These results show that the pH decrease observed during sterilization can be minimized by inclusion of a buffering agent. In addition, the data shows that of the buffering systems tested, acetate showed the lowest viscosity decrease as a result of sterilization.

Example 2

Example 1 was repeated, but this time using the following buffering agents in the indicated concentrations:

Propionic acid (0.1M)
Fumaric acid (0.05M)
Succinic acid (0.1M)
Crotonic acid (0.1M)
Sodiumhydrogen tartrate (0.1M)
Sulphuric acid (0.1M)
Ascorbic acid (0.1M)
Sodium benzoate (0.1M)
Boric acid (0.1M)
Monoethanol amine (0.1M)

It was found that pH stability of the compositions containing sulphuric acid or monoethanol amine was unacceptable. Furthermore, the compositions containing boric acid, ascorbic acid or monoethanol amine were found to suffer from unacceptable viscosity fluctuations during heat sterilisation. The pH- and viscosity stability of the other alginate-based compositions was acceptable. Of these compositions, the alginate-based compositions containing sodium benzoate, crotonate or succinate performed best.

Example 3

An alginate-based buffered aqueous composition (100 ml) was prepared on the basis of the following recipe, using the methodology described in example 1 (under an inert atmosphere of $N_2$ to avoid absorption of $CO_2$ from ambient air). This time, however, the pH of the aqueous compositions was set to 7.0 prior to sterilization

| Ingredient | Amount |
|---|---|
| Sodium alginate | 2000 mg |
| Dextran sulphate | 53.8 mg |
| NaCl | 800 mg |
| Sodium acetate | 500 mg |
| Sodium bicarbonate | 0-50 mg |
| Water | Remainder (to 100 ml) |

To investigate long-term stability as well as the robustness of the pH stabilization, the pH was determined after 30 and 60 minutes of sterilization. Four formulations containing different amounts of carbonate were subjected to the identical sterilization conditions (see Example 1). The results obtained are depicted in the following table.

| Amount of sodium bicarbonate | pH after 30 minutes sterilization | pH after 60 minutes sterilization | Specification 6.5-7.5 |
|---|---|---|---|
| 0 mg | 6.8 | 6.0 | Out of spec |
| 9 mg | 7.2 | 7.1 | Within spec |
| 36 mg | 7.7 | 7.5 | Within spec |
| 50 mg | 8.0 | 7.8 | Out of spec |

These results show that the formulation with the lowest carbonate addition (9 mg) yields the most stable pH profile. Even after a steam sterilization cycle of 60 minutes, the pH stays within a pH range of 6.5-7.5.

Example 4

The formulation described in Example 3 containing 500 mg of sodium acetate and 9 mg of sodium bicarbonate was used in a series of experiments designed to test the influence of $CaCl_2$ cross-linking on pH stability and viscosity. The influence of different concentrations of $CaCl_2$ on pH immediately after sterilization is depicted in the following table.

| Amount of $CaCl_2$ | pH increase after 30 minutes sterilization |
|---|---|
| 0 mg | 0.27 |
| 33 mg | 0.22 |
| 66 mg | 0.23 |
| 99 mg | 0.37 |

In addition, the stability of these formulations during storage was tested. The samples were put in thermostatic ovens at different temperatures. pH was measured at regular intervals over a period of 3 months. The results are represented in the following tables.

| | | pH | | | | | |
|---|---|---|---|---|---|---|---|
| $CaCl_2$ | Temperature | pre-sterilization | 0 weeks | 4 weeks | 8 weeks | 12 weeks | specification 6.5-7.5 |
| 99 mg | 4° C. | 6.9 | 7.5 | 7.2 | 7.0 | 7.0 | within spec |
| | 25° C. | 7.1 | 7.4 | 7.4 | 7.1 | 7.0 | within spec |
| | 40° C. | 6.9 | 7.3 | 7.1 | 7.2 | 6.9 | within spec |
| | 60° C. | 7.0 | 7.3 | 7.0 | 7.7 | 8.0 | out of spec |
| 66 mg | 4° C. | 6.8 | 7.0 | 7.2 | 7.0 | 7.2 | within spec |
| | 25° C. | 6.9 | 7.7 | 7.2 | 6.9 | 7.2 | within spec |
| | 40° C. | 7.0 | 7.3 | 7.2 | 7.2 | 6.9 | within spec |
| | 60° C. | 7.0 | 7.7 | 8.7 | 8.1 | 6.9 | out of spec |
| 33 mg | 4° C. | 6.9 | 7.1 | 7.1 | 6.9 | 7.1 | within spec |
| | 25° C. | 6.9 | 7.2 | 6.9 | 6.8 | 6.9 | within spec |
| | 40° C. | 7.0 | 7.2 | 7.2 | 7.0 | 7.1 | within spec |
| | 60° C. | 6.9 | 7.0 | 7.1 | 7.0 | 7.6 | out of spec |
| 0 mg | 60° C. | 6.9 | 7.2 | 7.8 | 8.5 | 7.6 | out of spec |

Furthermore, for the viscosity of the formulations was monitored over a three month storage period (at 60° C.), yielding the following results:

| | Viscosity in cP | | | |
|---|---|---|---|---|
| $CaCl_2$ | 0 weeks | 4 weeks | 8 weeks | 12 weeks |
| 99 mg | 5000 | 2300 | 1800 | 1400 |
| 66 mg | 3850 | 1830 | 1990 | 1010 |
| 33 mg | 1500 | 800 | 650 | 750 |
| 0 mg | 1950 | 550 | 450 | 500 |

These results show that moderate cross linking with calcium ions (33 mg or 66 mg $CaCl_2$) gives increased pH stability and improved viscosity stability.

Example 5

In order to investigate the possible influence of alginate molecular weight (Mw) characterised by viscosity on pH stability, two alginate salts having different molecular weight distributions were tested, one high molecular weight alginate (Manugel DMB, FMC Biopolymer, viscosity 300 cP 1% solution) and one low molecular weight alginate (Manugel LBA, FMC Biopolymer, viscosity 700 cP 10% solution). Formulations were prepared using the methodology described in example 1 and subjected to sterilization times of 0 to 100 minutes. The pH of the formulations was monitored during sterilization. The results obtained showed that the pH of the formulation containing the high molecular weight alginate varied by no more than 0.3 pH units from the initial pH. The formulation containing the low molecular weight alginate showed a pH drift of 0.7 pH units.

Example 6

Anti-adhesion compositions for surgical use should be physiologically acceptable and hence preferably should not be hyper or hypo-osmotic. An anti-adhesion composition having an osmolality of 280-295 mOsm/l was prepared on the basis of the following recipe, using the methodology described in Example 1.

| Ingredient | mg/ml (anhydrous) |
|---|---|
| Polydextran sulphate | 0.525 |
| Alginate | 20 |
| NaCl | 4.6 |
| $NaCO_2CH_3$ | 5 |
| $NaHCO_3$ | 0.0833 |
| $CaCl_2$ | 0.33 |

This composition was prepared under GMP conditions in three independent production runs (three batches), filled into 100 mL syringes and sterilised at 121° C. for 15 minutes. After sterilisation, of each batch, an adequate amount of syringes was tested on pH, viscosity, osmolality, assay sodium alginate, assay polydextran sulphate, assay of calcium, endotoxins and sterility. All parameters were within preset specifications. The three batches were then stored to perform a stability study, according to ICH Guidance, at 25° C., 60% relative humidity and tested on pH and viscosity (visc.) after 0 (initial), 3, 6, 12 and 18 months storage. The results were as follows:

| | | Shelf life specifications | Initial | 3 months | 6 months | 12 months | 18 months |
|---|---|---|---|---|---|---|---|
| pH | Batch-1 | 6.5-7.5 | 6.9 | 6.8 | 6.9 | 7.1 | 7.1 |
| | Batch-2 | 6.5-7.5 | 7.0 | 7.0 | 6.9 | 7.1 | 7.0 |
| | Batch-3 | 6.5-7.5 | 6.9 | 6.9 | 7.0 | 7.1 | 7.0 |
| Visc. | Batch-1 | 1000-10.000 (mPa · s) | 3100 | 2843 | 3010 | 3050 | 3010 |
| | Batch-2 | 1000-10.000 (mPa · s) | 3718 | 3815 | 3566 | 3684 | 3899 |
| | Batch-3 | 1000-10.000 (mPa · s) | 2950 | 2915 | 3010 | 3025 | 3000 |

The invention claimed is:

1. A sterile aqueous composition having a viscosity at 25° C. of at least 300 cP (Helipath® T F spindle, 100 rpm at 25° C.) and a pH in the range of 6.5-7.5, the composition comprising 0.5-10 wt. % of an alginate salt and 10-500 mM of one or more dissolved $C_2$-$C_7$ mono- or dicarboxylates that are optionally substituted with up to 2 hydroxyl groups.

2. The aqueous composition according to claim 1, having a viscosity at 25° C. of less than 10,000 cP.

3. The aqueous composition according to claim 2, having a viscosity at 25° C. of 500-8,000 cP.

4. The aqueous composition according to claim 1, comprising 1-5 wt. % of the alginate salt.

5. The aqueous composition according to claim 1, wherein the alginate salt has a molecular weight of at least 50,000 g/mol.

6. The aqueous composition according to claim 5, wherein the alginate salt has a molecular weight of at least 400,000 g/mol.

7. The aqueous composition according to claim 1, wherein the alginate salt is cross-linked by divalent cations selected from $Ca^{2+}$, $Mg^{2+}$ and combinations thereof.

8. The aqueous composition according to claim 7, wherein the total content of divalent cations selected from $Ca^{2+}$, $Mg^{2+}$ and combinations thereof is within the range of 10-3000 μmol per gram of alginate.

9. The aqueous composition according to claim 8, wherein the total content of divalent cations selected from $Ca^{2+}$, $Mg^{2+}$ and combinations thereof is within the range of 20-1200 μmol per gram of alginate.

10. The aqueous composition according to claim 1, wherein the one or more $C_2$-$C_7$ mono- or dicarboxylates are saturated or unsaturated, linear $C_2$-$C_4$ mono- or dicarboxylates that are optionally substituted with up to 2 hydroxyl groups.

11. The aqueous composition according to claim 1, wherein the one or more $C_2$-$C_7$ mono- or dicarboxylates are represented by the following formula:

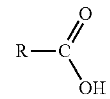

wherein R represents $R^1(R^2)CH$; $R^3$—CH═CH or phenyl;
$R^1$ representing hydrogen or hydroxyl;
$R^2$ representing hydrogen or $R^4(R^5)CH$;
$R^3$ representing methyl or COOH;
$R^4$ representing hydrogen or hydroxyl; and
$R^5$ representing hydrogen or COOH.

12. The aqueous composition according to claim 11, wherein R represents $R^1$ $(R^2)CH$.

13. The aqueous composition according to claim 11, wherein $R^1$ represents hydrogen; and $R^2$ represents hydrogen, $CH_3$, $CH_2COOH$ or CH(OH)COOH.

14. The aqueous composition according to claim 11, wherein R represents phenyl.

15. The aqueous composition according to claim 11, wherein R represents $R^3$—CH═CH.

16. A process for preparing an aqueous composition according to claim 1, comprising (a) combining a water-soluble alginate salt; the one or more $C_2$-$C_7$ mono- or dicarboxylates and water, and (b) sterilizing the composition.

17. The process according to claim 16, comprising combining an aqueous solution of 6-120 g/l of the water-soluble alginate salt with an aqueous solution containing 3-250 mmol/l of divalent cations selected from $Ca^{2+}$, $Mg^{2+}$ and combinations thereof.

18. The process according to claim 17, wherein the aqueous solution of the water-soluble alginate salt and the aqueous solution of the divalent cations are combined in a weight ration between 1:2 to 10:1.

* * * * *